(12) United States Patent
Hörle et al.

(10) Patent No.: US 9,889,049 B2
(45) Date of Patent: Feb. 13, 2018

(54) ABSORBENT PRODUCT

(71) Applicant: SCA Hygiene Products AB, Göteborg (SE)

(72) Inventors: Magdalena Hörle, Göteborg (SE); Angelica Burvall, Bollebygd (SE)

(73) Assignee: SCA HYGIENE PRODUCTS AB, Göteborg (SE)

( * ) Notice: Subject to any disclaimer, the term of this patent is extended or adjusted under 35 U.S.C. 154(b) by 0 days.

(21) Appl. No.: 15/308,849

(22) PCT Filed: May 15, 2014

(86) PCT No.: PCT/SE2014/050589
§ 371 (c)(1),
(2) Date: Nov. 4, 2016

(87) PCT Pub. No.: WO2015/174896
PCT Pub. Date: Nov. 19, 2015

(65) Prior Publication Data
US 2017/0071799 A1    Mar. 16, 2017

(51) Int. Cl.
*A61F 13/15* (2006.01)
*A61F 13/472* (2006.01)
(Continued)

(52) U.S. Cl.
CPC .. *A61F 13/47245* (2013.01); *A61F 13/15203* (2013.01); *A61F 13/45* (2013.01);
(Continued)

(58) Field of Classification Search
CPC ............... A61F 13/45; A61F 13/4704; A61F 13/15804; A61F 13/15617; A61F 13/53;
(Continued)

(56) References Cited

U.S. PATENT DOCUMENTS 2,408,508 A    10/1946  Canavan
D234,162 S     1/1975   Andersen
(Continued)

FOREIGN PATENT DOCUMENTS

DE    29915071 U1    2/2000
EP    0159671 A2     10/1985
(Continued)

OTHER PUBLICATIONS

U.S. Appl. No 15/308,847, filed Nov. 4, 2016, Magdalena Hörle et al.
(Continued)

*Primary Examiner* — Jacqueline Stephens
(74) *Attorney, Agent, or Firm* — Drinker Biddle & Reath LLP (57) ABSTRACT

An absorbent product including a liquid-permeable top layer, a liquid-impermeable bottom layer and an absorbent core arranged between the top layer and the bottom layer is disclosed. The absorbent product has a head product portion, an intermediate product portion and a rear product portion extending in a longitudinal direction of the absorbent product. The absorbent product has an outer contour having a shape resembling an hourglass, wherein the intermediate product portion includes an area with a smaller width than any area in the head product portion and rear product portion, respectively, and wherein the core extends in the longitudinal direction and transverse direction of the absorbent product and has an outer contour that is asymmetrical with the outer contour of the absorbent product.

19 Claims, 2 Drawing Sheets

(51) Int. Cl.
*A61F 13/45* (2006.01)
*A61F 13/511* (2006.01)
*A61F 13/514* (2006.01)
*A61F 13/53* (2006.01)
*A61F 13/56* (2006.01)

(52) U.S. Cl.
CPC ...... *A61F 13/472* (2013.01); *A61F 13/51121* (2013.01); *A61F 13/51405* (2013.01); *A61F 13/53* (2013.01); *A61F 13/5605* (2013.01); *A61F 2013/15373* (2013.01); *A61F 2013/15422* (2013.01); *A61F 2013/530007* (2013.01); *A61F 2013/5307* (2013.01); *A61F 2013/530481* (2013.01); *A61F 2013/530802* (2013.01)

(58) Field of Classification Search
CPC ............ A61F 13/472; A61F 2013/4708; A61F 2013/530802; A61F 2013/530007; A61F 2013/530481
See application file for complete search history.

(56) References Cited

U.S. PATENT DOCUMENTS

| | | | |
|---|---|---|---|
| 6,350,257 B1 * | 2/2002 | Bjorklund | A61F 13/4702 604/385.01 |
| 6,632,210 B1 | 10/2003 | Glasgow et al. | |
| 6,965,058 B1 | 11/2005 | Raidel et al. | |
| 2008/0103468 A1 | 5/2008 | Elfsberg et al. | |
| 2010/0152687 A1 | 6/2010 | Carlozzi | |
| 2017/0071798 A1 | 3/2017 | Hörle et al. | |

FOREIGN PATENT DOCUMENTS

| | | |
|---|---|---|
| EP | 0670153 A1 | 9/1995 |
| EP | 1138294 A1 | 10/2001 |
| EP | 1260205 A2 | 11/2002 |
| EP | 1757257 A2 | 2/2007 |
| EP | 1994917 A1 | 11/2008 |
| GB | 2282541 A | 4/1995 |
| JP | 2001-504724 A | 4/2001 |
| JP | 2009-501053 | 1/2009 |
| WO | WO-97/39713 A1 | 10/1997 |
| WO | WO-98/22057 A1 | 5/1998 |
| WO | WO-99/25282 A1 | 5/1999 |
| WO | WO-01/35888 A1 | 5/2001 |
| WO | WO 2007/008125 A1 | 1/2007 |
| WO | WO-2007/069957 A1 | 6/2007 |

OTHER PUBLICATIONS

Extended European search report dated Oct. 24, 2017 issued in related European patent application No. 14 89 2150 (7 pages).

Extended European search report dated Oct. 4, 2017 issued in corresponding European patent application No. 14 891 809.7 (7 pages).

Japanese Notice of Reasons for Rejection dated Sep. 25, 2017 issued in corresponding Japanese patent application No. 2016-567037 (4 pages) and its English-language translation thereof (4 pages).

* cited by examiner

ABSORBENT PRODUCT

CROSS-REFERENCE TO PRIOR APPLICATION

This application is a §371 National Stage Application of PCT International Application NO. PCT/SE2014/050589 filed May 15, 2014, which is incorporated herein in its entirety.

TECHNICAL FIELD

The present disclosure relates to an absorbent product, such as a panty liner. The absorbent product includes a liquid-permeable top layer, a liquid-impermeable bottom layer and an absorbent core arranged between the top layer and the bottom layer. The absorbent core includes an absorbent material with absorbent characteristics and a superabsorbent material. The product has a first extension in a longitudinal direction and a second extension in a transverse direction. The product has a longitudinal central line extending through the product and located between a first longitudinal portion and a second longitudinal portion of the product. The first and second longitudinal portions are symmetrical about the longitudinal central line. The product has a head portion, an intermediate portion and a rear portion extending in a longitudinal direction of the product. The product has an outer contour having a shape resembling an hourglass, wherein the intermediate portion includes an area with a smaller width than any area in the head portion and rear portion respectively. The core extends in the longitudinal direction and transverse direction of the product and has an outer contour that is asymmetrical with the outer contour of the product.

BACKGROUND

Panty liners are absorbent products that are used to absorb small amounts of bodily fluids such as urine and blood. Panty liners are smaller in size than sanitary towels or incontinence pads and are intended to be used for everyday freshness and to protect lingerie, i.e. briefs. There are several kind of briefs on the market today: traditional briefs that have a crotch portion that is relatively broad, hipster-type of briefs that have a relatively narrow crotch portion and thong-type briefs that have a very narrow crotch portion followed by an even narrower rear portion so as to expose all or significant portion of the buttocks of the user. Due to many different brief models it has been difficult in the prior art to optimize the shape and size of the panty liners such that a reliable protection is obtained while the panty liner is comfortable and discreet to wear.

There have been several attempts in the prior art to solve problems with adapting the absorbent products to thong-type briefs. EP1757257 A2 and EP 1138294, respectively, disclose panty liners comprising a core which is adaptable to thong-type briefs. However, while these products may be adaptable to thong-type briefs, they do not provide an optimal comfort and feeling of secure protection when used with traditional briefs or with hipster-type briefs, since neither the shape of the absorbent product itself nor the shape of the core conforms to the anatomy of the user or is shaped to be adapted to that kind of underwear. Thus, there is a need for an absorbent product that can be worn with different types of underwear while optimal comfortability and protection can be provided.

SUMMARY

It is desired to provide an obtained absorbent product, such as a panty liner, where the previously mentioned problems are avoided. It is also desired to provide an absorbent product that can be worn with different types of underwear while optimal comfortability and protection can be provided.

As used herein, the term "panty liner" means an absorbent product which is used for feminine hygiene and which is narrower than sanitary napkins. Panty liners absorb less liquid than sanitary napkins and are thus aimed for light bodily discharge and for everyday cleanliness. The product disclosed herein includes a liquid-permeable top layer, a liquid-impermeable bottom layer and an absorbent core arranged between the top layer and the bottom layer. The absorbent core includes an absorbent material with absorbent characteristics and a superabsorbent material. The product has a first extension in a longitudinal direction and a second extension in a transverse direction. The product has a longitudinal central line extending through the product and located between a first longitudinal portion and a second longitudinal portion of the product. The first and second longitudinal portions are symmetrical about the longitudinal central line. The product has a head portion, an intermediate portion and a rear portion extending in a longitudinal direction of the product. The product has an outer contour having a shape resembling an hourglass, wherein the intermediate portion includes an area with a smaller width than any area in the head portion and rear portion, respectively. The core extends in the longitudinal direction and transverse direction of the product and has an outer contour that is asymmetrical with the outer contour of the product.

The head portion of the product includes:
- a foremost point of the product in the longitudinal direction at the point where the central line of the product crosses the outer contour of the product;
- a first product width extending between two opposing outermost points on the outer contour of the product in the transverse direction, the first product width being the broadest in the product; and
- a first core width extending between two opposing outermost points of the outer contour of the core in the transverse direction, the first core width being the broadest in the core.

The head portion transitions to the intermediate portion at intermediate transition points of the product and second transition points of the core. The core has a second core width in the transverse direction extending between two opposing second transition points of the core, the second width being smaller than the first core width.

The intermediate portion of the product includes:
- a second product width extending between two opposing points in the area of the product having the smallest width, which second product width is longitudinally distanced from the second core width; and
- a third core width extending between two opposing outermost points of the intermediate portion of the core, the third core width being broader than the second core width.

The intermediate portion transitions to the rear portion at rear transition points of the product and at third transition points of the core.

The rear portion of the product includes:
- a third product width which is broader than the second product width,
- a rear portion of the core tapering towards a rear end point which is longitudinally distanced from the rear end point of the product, and wherein
- a point on the outer contour of the product, which has the largest distance to the outer contour of the core.

By the feature of a point on the outer contour of the product having the largest distance to the outer contour of the core is meant that a perpendicular line that crosses a tangent of the point on the outer contour of the product and which perpendicular line crosses a point on the outer contour of the core has a largest distance in the rear portion of the product.

One advantage with an absorbent product with the described shape is that it is suitable for use with most types of briefs, for instance thong-type briefs, traditional briefs and hipster-type briefs while optimal comfort and conformance to the wearer's body can be provided.

The shape of the absorbent product has been found to fit the various widths of the crotch portions of for instance thong-type briefs, traditional briefs and hipster-type briefs while still providing a good absorption capacity, good coverage of the crotch portion of the underwear to avoid the undergarment to become soiled during use and comfort due to the shape of the core together with the shape of the complete product. The outer contour of the product follows the curvature of the crotch portion of the briefs. In the case of thong-type briefs or briefs with a tapering or narrow rear crotch portion, the shape of the product allows the rear portion of the product to be folded round the edges of the briefs, similar to a product with wings, in order to secure the product to the briefs. In the traditional briefs the absorbent product covers the crotch portion, while in the hipster-type briefs the absorbent product may extend out to the edges and beyond the edges of the crotch portion of many hipster-type briefs.

The core, having an asymmetrical shape compared with the shape of the outer contour of the product, i.e. which is not resembling an hourglass shape, is designed to follow the shape of the body and fit snugly between the thighs of the user. The absorbent product according to embodiments described herein, besides being suitable to wear with all kinds of briefs, protects the briefs from getting wet and is comfortable to the skin.

The ratio of the thickness between the edge area of the product and the core is from 1:35 to 1:3. The thickness of the core is from 1.5 to 3.4 mm, or from 2.2 to 3.0 mm and the thickness of the edge area of the product is 0.1 to 0.3 mm. An absorbent product according to embodiments described herein has a high absorption capacity while being soft and comfortable against the skin of a user. The thin edge area ensures that it is easy to fold the edge area around the crotch portion of the briefs if necessary, it is less noticeable and due to its thinness creates high comfort to the wearer.

A shape resembling an hourglass is a shape which is wide at the ends of the product and narrows towards the middle of the product. The shape resembling an hourglass may be a symmetric or essentially symmetric shape wide at its ends and narrow in the middle. The outer contour of the product may be an asymmetrical hourglass-shaped contour, wherein the outer contour of the product includes in the intermediate portion a first concave arch-shaped portion having a first radius which transitions to a second arch-shaped portion having a second radius, wherein the first radius is smaller than the second radius. A shape resembling an hourglass is a symmetric or essentially symmetric shape wide at its ends and narrow in or close to the middle.

The top layer may include a nonwoven material, being a spunbond material including polypropylene fibres. The top layer may alternatively consist entirely of a nonwoven material, being a spunbond material including polypropylene fibres.

The absorbent product may additionally include an acquisition layer located beneath the top layer. The acquisition layer is intended to quickly absorb liquid and disperse the liquid before it is transported to the absorbent core, where it is retained. The acquisition layer can include low density airlaid or wadding.

The head portion of the core may include in the respective first and second longitudinal portions mirror imaged:
  a. first circular segment portions extending in a longitudinally forward direction of the core from a first transition point, located on the central line between the circular segment portions, in an acute angle $\beta$ between the central line and a tangent at a point of transition point in respect of the circular segment portion, and
  b. first edge lines, to which the circular segment portions transition, tapering towards the intermediate portion and towards the central line of the core in an angle $\alpha$ being from 15-45°, and wherein the first edge lines taper to a second transition point located between the head portion and the intermediate portion.

The intermediate portion of the core may include, in the respective first and second longitudinal portions; mirror imaged first convex edge portions extending between the second transition points and third transition points which third transition points are located between the intermediate portion and the rear portion, wherein the convex edge portions have a length of from 50-60% of the total length of the central line and have a maximum height of the arch in the transverse direction of the core of from 1-10 mm.

The rear portion may include second edge lines tapering towards a rear end point and the central line of the core in an angle being from 3-20°. The second edge lines taper to a fourth transition point from which the second edge lines transition to a rear end portion that joins the edge lines together. In a particular embodiment, the rear end portion is semi-circular or has a shape of circular segment, thus providing a comfortable shape during use.

One advantage with an absorbent core having a shape as described above is that the core is suitable for use in an absorbent product according to embodiments described herein and thus suitable for use with many types of briefs. The shape of the absorbent core has been found to fit the various widths of the crotch portions of for instance thong-type briefs, traditional briefs and hipster-type briefs. When used in an absorbent product according to embodiments described herein-the core provides a good absorption capacity and comfort and a secure feeling of protection.

The total length of the product between the front end point and the rear end point of the product is from 130 to 175 mm, from 140 to 160 mm, or 150 mm. This product length has been found to be optimal for use in panty liners, such that maximal protection can be provided while the absorbent product can be placed discretely in most briefs. The length of the absorbent product further ensures that the product is long enough so that the core of the absorbent product does not move away from the intended position in the crotch portion of the briefs.

In one embodiment, the longitudinal extension of the head portion is about ⅓ of the extension of the product along the central line, the extension of the intermediate portion is about ⅓ of the extension of the product along the central line and the extension of the rear portion is about ⅓ of the extension of the product along the central line. These dimensions provide for an optimal shape for the absorbent product.

Suitably, the longitudinal extension of the head portion along the central line is from 40 to 50 mm, the extension of the intermediate portion is about 45-60 mm of the extension of the product and the extension of the rear portion is about 40-50 mm of the extension of the product. These dimensions provide for an optimal shape for the absorbent product.

The first product width of the product in the head portion is from 64-72 mm, or from 66 to 70 mm. This width provides for maximal protection and adaptation to the shape of the underwear.

The second product width in the intermediate portion is from 42-50 mm, or from 44 to 48 mm. In this way, a narrower portion is provided in the absorbent product which improves the adaptation to the wearer, e.g. to the thighs of the wearer. Also, the product as well as the core is easier to fold in transverse direction in this narrower portion making the product easier to handle. Also, in this way the product follows the underwear behaviour when the underwear is pulled up.

The third product width in the rear portion of the product is from 55 to 63 mm, or from 57 to 61 mm. This wider portion enables the rear portion to be folded round the rear crotch portion of for instance thong-type briefs.

The dimensions and the geometrical design of the absorbent product that follows with the dimensions described above have been found to advantageously ensure that the absorbent product can be placed in a desired location and cover the crotch portion of the briefs where discharge of for instance menstrual fluid or urine occurs regardless of the type of briefs worn by the user. The absorbent product according to embodiments described herein ensures that the core remains intact within the crotch area of the brief independent of the brief type when used in an absorbent product, i.e. the core fits within the crotch region of each briefs type and is subjected to minimal stress from the movements of the user.

The amount of the superabsorbent material in the core is from 10 to 30% by weight of the total weight of the absorbent core, or from 15 to 20% by weight. The amount of superabsorbent material ensures a good absorption capacity while maintaining a soft and comfortable core. The density of the core is from about 100 to 180 kg/m3, or from 120 to 145 kg/m3. The density of the core makes the core pliable and allows the core to easily follow the body of a wearer. An absorbent core according to embodiments described herein is capable of handling of at least 5 ml of menstrual fluid and is therefore suitable for everyday freshness use.

The core may include cellulosic fluff pulp, tissue, absorbent foam materials or absorbent nonwoven materials as the absorbent material. Preferably, the core comprises of cellulosic fluff pulp, which is easy to process and thus makes the core easy to manufacture while very good absorption capacity can be provided.

The area of the product in which the core is positioned may be embossed with a pattern that principally follows the design of the core. The embossing can be made in a variety of ways such as continuous pattern or discontinuous pattern, and in particular embodiments discontinuous. The embossing may for instance be made to steer and improve the flexibility of the core and to control and improve the fluid acquisition.

The bottom layer may include a sprayed adhesive coating on the side facing away from the body facing side of the product on which a release paper is attached. The sprayed adhesive coating can be sprayed onto the entire body facing side of the product although in practice a small area needs to be free from adhesive in order for a user to be able to remove the release paper from the product before placing the absorbent product in the briefs. Sprayed adhesive coating gives a good adhesion to the bottom layer which leads to that the product is not torn apart when removed from the briefs after use. Sprayed adhesive coating at the same time gives a good adhesion to the briefs ensuring that the product stays in place during use.

DETAILED DESCRIPTION OF PARTICULAR EMBODIMENTS

Figure 1:
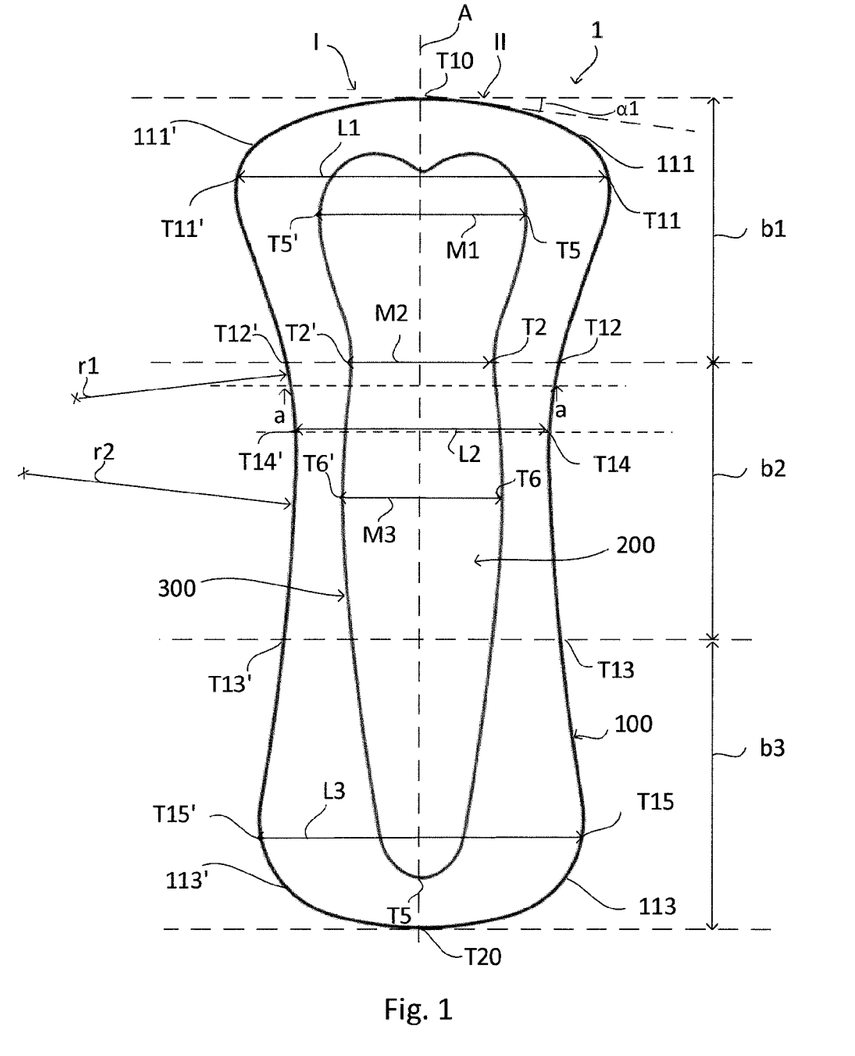
FIG. 1 schematically shows an absorbent product according to an embodiment.

FIG. 1 is a schematic view of an absorbent product 1 in accordance with an embodiment of the present invention, viewed from the above. The absorbent product 1 includes a first covering layer in the form of a liquid-permeable top layer 2 (shown in FIG. 2) which is arranged on the side of the absorbent product 1 which, during use, is intended to face towards the wearer. The absorbent product 1 also includes an absorbent core 3 including an absorbent material with absorbent characteristics and a superabsorbent material, arranged between the top layer 2 and a second covering layer in the form of liquid-impermeable bottom layer 4 (shown in FIG. 2). The liquid-impermeable bottom layer 4 is arranged on the side of the absorbent product 1 which, during use, is intended to face away from the wearer.

Figure 2:
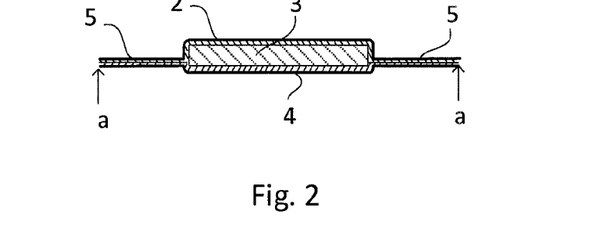
FIG. 2 schematically shows a cross section of the absorbent product along the line a-a in FIG. 1.

The liquid-permeable top layer 2 can be manufactured from a material that exhibits characteristics such as dryness and softness during the time when the absorbent product 1 is being worn, because this top layer is in contact with the wearer's body. It is also desirable for the top layer to have a soft and textile-like surface which remains dry, even in the event of repeated wetting. The top layer can include a nonwoven material, for example, with a soft and smooth surface, such as a spunbond material made from polypropylene fibres. A perforated, hydrophobic nonwoven material may be used in order to permit the surface that is closest to the wearer's body to be kept dry, in conjunction with which openings are formed in the material that are larger than the holes between the fibres in the material. In this way, liquid can be led down through the perforated openings in the top layer to the subjacent absorbent core. Other examples of materials for the top layer are perforated plastic films such as a perforated polyester film. The top layer can be joined together with the subjacent bottom layer and the absorbent core, for example by means of adhesive, ultrasonic jointing or by means of some form of thermal bonding. The nonwoven part of the top layer can also be a spunbond nonwoven material, an air-thru nonwoven material, a spunlace nonwoven (hydroentangled) material, a meltblown nonwoven material, or a combination of these. The raw material can be polypropylene (PP), polyethylene (PE) polyester (PET), polyamide (PA), or a combination of these. If a combination is used, this can be a mixture of fibres from different polymers, although each fibre can also include different polymers (e.g. PP/PE bi-component fibres or PP/PE copolymers). Where appropriate, the plastic film can include PE or PP, PET, PLA or amyl (or, for that matter, any other thermoplastic polymer), or a mixture or copolymers of the aforementioned polymers. The top layer can be a spunbond material including polypropylene fibres which provide for optimal comfort and handleability of the product. Other suitable fibres for making the nonwoven material are for example natural fibres such as bamboo, cotton and flax.

The absorbent core 3 is appropriately manufactured from a suitable fibre material in the form of natural or synthetic fibres with absorbent characteristics, or a mixture or natural fibres and synthetic fibres or other absorbent materials of a previously disclosed kind that are suitable for use in, for example, sanitary towels, incontinence pads and panty liners. The absorbent core 3 can also include a predetermined proportion, for example 10-30%, of superabsorbent material, that is to say polymer materials in the form of particles, fibres, flakes or the like, which possess the ability to absorb and chemically bind liquid equivalent to several times their own weight to form an aqueous gel. This imparts a very high liquid-absorbent capacity to the finished absorbent product 1 while the product 1 is still soft and easy to handle and manufacture.

The absorbent core 3 can be of a unitary construction. By "unitary construction" in the present context is meant that the absorbent core 3 is constructed from essentially one type of material, this being essentially the same material, or essentially the same combination of two or more materials throughout the absorbent core 3. Variations in density and concentration of the material may occur, but these are limited to those which may be obtained without incorporation of regions which have been formed separately and then physically joined to each other. For example, when the absorbent core 3 includes a matrix of an absorbent material with absorbent characteristics, e.g. hydrophilic fibres, and superabsorbent material, the relative concentrations of superabsorbent material and fibres may be different in different parts of the core 3. The absorbent material could also be a hydrophobic material that has the capability to retain liquid within the structure of the material. However, when the construction is unitary, the absorbent core 3 does not, for instance, include layers or laminates of different composition. Likewise, variations in the density or concentration of various components across the longitudinal direction, the transverse direction or the thickness direction of the absorbent core 3 may occur, yet the core 3 should not include areas or layers of different composition which are formed separately and later joined together.

The area of the product in which the core 3 is positioned is embossed with a pattern 200 that principally follows the design of the core 3. The embossing pattern includes discrete circular points which are arranged in a pattern that follows the design of the core 3. Other designs are of course possible. The bottom layer 4 can be liquid-impermeable (or should at least possess high resistance to penetration by liquid) and is thus so arranged as to prevent any leakage of excreted fluid from the absorbent product 1. The bottom layer 4, on the other hand, may be executed so that it is vapour-permeable. For this purpose, the bottom layer 4 may be manufactured from a liquid-impermeable material which can include a thin and liquid-proof plastic film. For example, plastic films of polyethylene, polypropylene or polyester can be used for this purpose. Alternatively, a laminate of nonwoven and plastic film or other suitable material layers can be used as a liquid-proof bottom layer 4. The underside of the bottom layer 4 can be provided with a sprayed adhesive coating (not illustrated), which can then be utilized for the attachment of the absorbent product 1 to an item of clothing.

The absorbent product 1 of FIG. 1 has a first extension in a longitudinal direction and a second extension in a transverse direction. The absorbent product 1 has a longitudinal central line A extending through the absorbent product 1 and located between a first longitudinal portion I and a second longitudinal portion II of the absorbent product 1, which first and second longitudinal portions I; II are symmetrical about the longitudinal central line A. The absorbent product 1 has a head product portion b1, an intermediate product portion b2 and a rear product portion b3 extending in a longitudinal direction of the absorbent product 1. The absorbent product 1 has an outer contour 100 having a shape resembling an hourglass. The intermediate product portion b2 includes an area with a smaller width than any area in the head product portion b1 and rear product portion b3, respectively. The absorbent core 3 extends in the longitudinal direction and transverse direction of the absorbent product 1 and has an outer contour 300 that is asymmetrical with the outer contour 100 of the absorbent product 1. The outer contour 300 is defined by the shape of core 3 which will be described in more detail below. The area between the outer contour 100 of the absorbent product 1 and the outer contour 300 of the absorbent core is defined as edge area 5. The edge area 5 includes the top layer 2 and the bottom layer 4. The top layer 2 and the bottom layer 4 extend beyond the edges of the absorbent core 3 and are joined to each other to form the edge area 5. This efficiently encapsulates the core 3 and prevents fibres, superabsorbent particles or similar to leak from the core 3.

The head product portion b1 of the absorbent product 1 includes a foremost point T10 of the absorbent product 1 in the longitudinal direction at the point where the central line A of the absorbent product 1 crosses the outer contour 100 of the absorbent product 1. The outer contour 100 includes first product circular segments 111, 111' extending from the foremost point T10 downward at an angle α1 towards two opposing outermost points T11; T11'. The angle α1 is defined as the angle between a transverse line perpendicular to the central line A and a tangent line of the first product circular segment portions 111; 111', where the tangent line is the tangent line at the transition point T10 of the respective first product circular segment portions 111; 111'. The angle α1 may be for example 1-10° or 2-7°.

The head portion further includes a first product width L1 extending between two opposing outermost points T11; T11' on the outer contour 100 of the absorbent product 1 in the transverse direction. The first product width L1 is the broadest in the absorbent product 1. A first core width M1 extends between two opposing outermost points T5; T5' of the outer contour 300 of the core 3 in the transverse direction, the first core width M1 being the broadest in the core. It is important that M1 has a sufficient width to ensure that the core is comfortable during use. The width should be sufficient to cover the labia and to not to glide in between the labia while the width should be small enough to not to extend outside the edges of the intended underwear. The width above has been found to fulfil these requirements. The head product portion b1 transitions to the intermediate product portion b2 at intermediate transition points T12; T12' of the absorbent product 1 and second transition points T2, T2' of the core 3. The core has a second core width M2 in transverse direction extending between the two opposing second transition points T2, T2' of the core. The second core width M2 is smaller than the first core width M1.

The outer contour 100 of the absorbent product 1 is an asymmetrical hourglass-shaped contour, wherein the outer contour 100 of the absorbent product 1 includes in the intermediate product portion b2 a first concave arch-shaped portion having a radius r1 which transitions to a second arch-shaped portion having a radius r2, wherein the radius r1 is smaller than the radius r2. The first product circular segments 111; 111' transition to the first concave arch-shaped portion at or slightly below the two opposing outermost points T11; T11'.

The intermediate product portion b2 of the absorbent product 1 includes a second product width L2 extending between two opposing points T14; T14' in the area of the absorbent product 1 having the smallest width. The second product width L2 is longitudinally distanced from the second core width M2. The intermediate product portion b2 further includes a third core width M3 extending between two opposing outermost points T6; T6' of the intermediate core portion a2, the third core width M3 being broader than the second core width M2. It is important that M3 has a sufficient width to ensure that maximum amount of the discharge lands on the core and not outside the core during use while the width should be small enough to not to extend outside the edges of the intended underwear. In this way leakage problems can be avoided. The intermediate product portion b2 transitions to the rear product portion b3 at rear transition points T13, T13' of the absorbent product 1, and at third transition points T3, T3' of the core 3.

The rear product portion b3 of the absorbent product 1 includes a third product width L3, extending from two opposing points T15; T15', which is broader than the second product width L2. A rear core portion a3 tapers towards a rear end point T5 which is longitudinally distanced from the rear end point T20 of the absorbent product 1. A point on the outer contour 100 of the absorbent product 1 has the largest distance to the outer contour 300 of the core, which means that a perpendicular line that crosses a tangent of a point on the outer contour of the product and which perpendicular line crosses a point on the outer contour of the core has a largest distance in the rear portion of the product. The second concave arch-shaped portion transition to second product circular segments 113; 113' at or slightly above the two opposing points T15; T15'. The second product circular segments 113; 113' joins at rear end point T20 to close the outer contour 100.

The core will be described in more detail below.

The longitudinal extension of the head product portion b1 can be about ⅓ of the extension of the absorbent product 1 along the central line A, the extension of the intermediate product portion b2 can be about ⅓ of the extension of the absorbent product 1 along the central line A and the extension of the rear product portion b3 can be about ⅓ of the extension of the absorbent product 1 along the central line A. More specifically, the longitudinal extension of the head product portion b1 along the central line A may be from 40 to 50 mm, the extension of the intermediate product portion b2 may be about 45-60 mm of the extension of the absorbent product 1 and the extension of the rear product portion b3 may be about 40-50 mm of the extension of the absorbent product 1.

The first product width L1 of the absorbent product 1 in the head product portion b1 is from 64-72 mm, or from 66 to 70 mm. The second product width L2 in the intermediate product portion b2 is from 42-50 mm, or from 44 to 48 mm. The third product width L3 in the rear product portion b3 of the absorbent product 1 is from 55 to 63 mm, or from 57 to 61 mm.

The first and second portions I; II are designed and arranged such that they are symmetric in respect to each other about the longitudinal centre line A of the core. This is important so that the core lies symmetrically on the user's body when in use. By the expression "symmetric about the longitudinal centre line A" it is herein meant that each point in the first or second portions on one side of the longitudinal centre line A has a corresponding point in the opposing side of the longitudinal centre line A; the two points being related to each other by reflection in a plane located on the longitudinal centre line A. The first longitudinal portion located on one side of the longitudinal centre line A is therefore the mirror image of the second longitudinal portion located on the other side of the longitudinal centre line A.

FIG. 2 schematically shows a cross section of the absorbent product along the line a-a in FIG. 1. The cross section schematically shows the relationship between the thickness of the core 3 and the thickness of the edge area 5, not to scale. The thickness of the core 3 is taken in the centre of the core 3. The thickness of the edge area 5 is taken at a point between the outer contour 100 of the absorbent product 1 and the outer contour of core 3. The thickness of the core 3 and of the outer edge 5 is measured using a thickness gauge. The thickness gauge and the method for using the thickness gauge are described below.

The gauge consists of:

Mitutoyo gauge with a data output. Resolution 0.01 mm (0.001 mm). Accuracy ±0.02 mm (±0.002 mm).

Speed reducing unit, intended for adjustment of the lowering speed of the measurement foot. Normal setting 13±1 mm/s.

Lever arm for adjustment of the load of the measurement plate. Normal load (pressure onto the product) is 0.5 kPa±0.002 kPa Measurement foot with different shape and area depending on measurement object.

Rollax device with 3 bearings, of which one is eccentric for adjustment of the axle.

Rollax device with one bearing.

Oil container, filled up to ⅓ with oil.

Oil that does not exert influence on the gaskets, e.g. ATF oil, Q8 auto 15.

| | |
|---|---|
| Density | 862 kg/m3 (at 15° C.) |
| Viscosity | 35.8 mm2/s (at 40° C.) |
| Viscosity | 8.0 mm2/s (at 100° C.) |
| Viscosity index | 200 |

Function

The thickness is determined by means of a measurement foot with a fixed load, which is lowered onto the sample at a given rate. The thickness is read off at the digital thickness gauge.

Functional check

Check of axle:

Raise the measurement foot to the upper level by lowering the hand-lever.

Lower the measurement foot by raising the hand-lever

Check visually that the axle moves steadily and smoothly downwards

Check of the piston of the digital thickness gauge:

Check visually that the piston of the digital thickness gauge, the moving metal rod, follows the lowering of the measurement foot, standing on the axle of the thickness gauge. The piston shall move easily up and down.

Check that the piston not has hollowed out the axle of the thickness gauge at the point of impact.

Check that there are no fibres or dust under the tip.

Check of the oil container:
 Check that there are no air bubbles in the oil. Air bubbles are removed by raising and lowering the hand-lever a couple of times.
Preparations
 Check that the instrument is calibrated and adjusted.
 Carry out Functional check.
Procedure
 Put the instrument on a plane foundation.
 Press the On/Off-button alt. On/Zero-button on the Mitutoyo gauge.
 Set to zero by pressing the Origin-button (2 s) alt. On/Zero-button when the measurement foot is lowered.
 * Raise the measurement foot to the upper level by lowering the hand-lever. Leave it in the upper level for at least 5 seconds, before it is lowered, to give the oil time to flow back into the cylinder.
 Put the sample under the measurement foot.
 Lower the measurement foot by raising the hand-lever, until the counter weight is set free. The foot should be lowered by its own weight.
 Read off the results after 5 seconds and raise the measurement foot to the top level.
 Next measurement: Repeat from *. End of method.

The ratio of the thickness between the edge area 5 of the absorbent product 1 and the core is from 1:35 to 1:3. More specifically, the thickness of the core 3 is from 1.5 to 3.4 mm, or from 2.2 to 3.0 mm and the thickness of the edge area of the absorbent product 1 is 0.1 to 0.3 mm.

Figure 3:
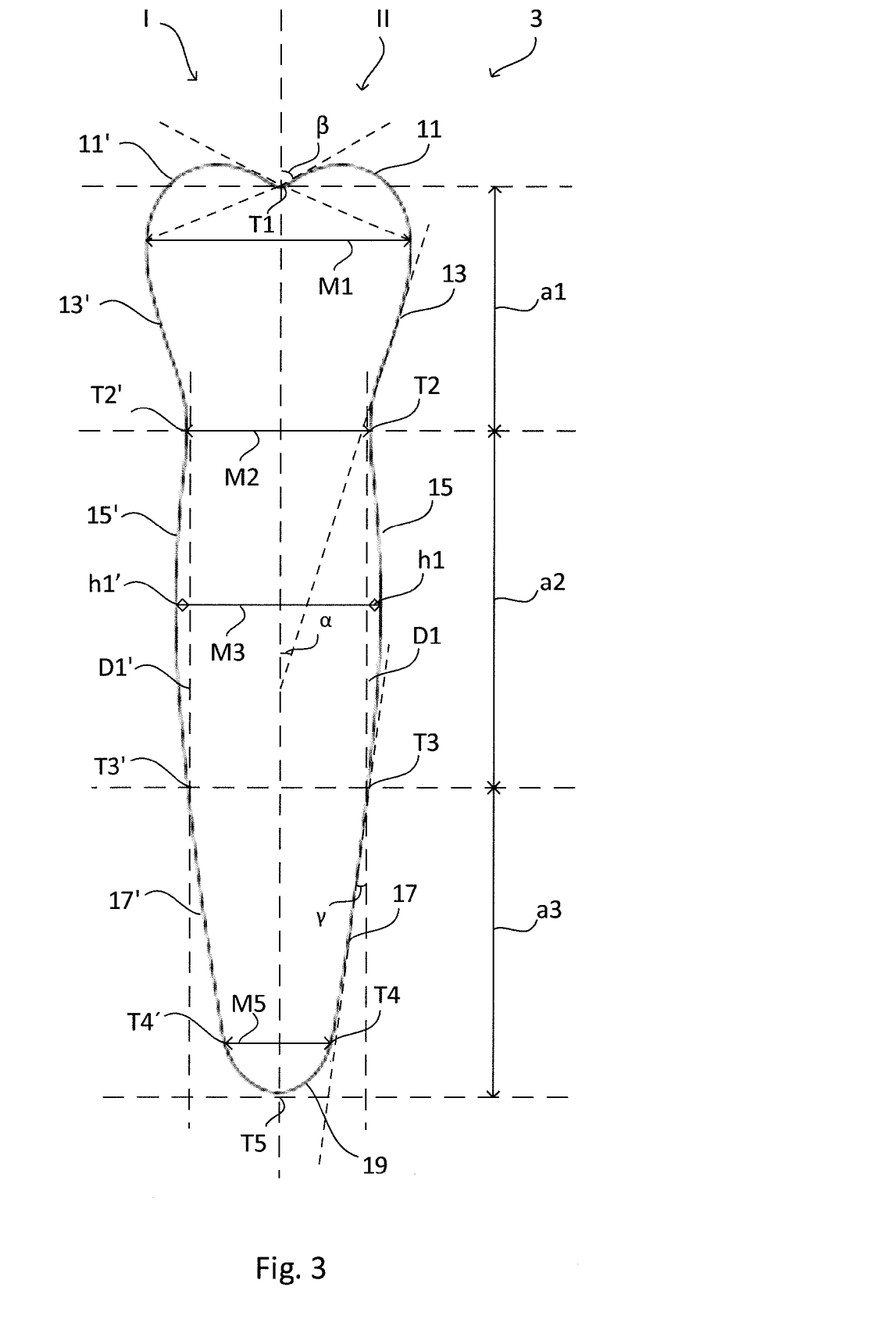
FIG. 3 schematically shows a core suitable for use with an absorbent product such as the one shown in FIG. 1.

FIG. 3 is a schematic view of an absorbent core 3 in accordance with the present invention, viewed from the above. A head core portion a1 comprises in the respective first and second longitudinal portions I; II mirror imaged first circular segment portions 11; 11' extending in a longitudinally forward direction of the core from a first transition point T1. A longitudinal forward direction of the core 3 is in the direction towards and over the head core portion a1. The first transition point T1 is located on the central line A in the intersection between the circular segment portions 11, 11'. The first circular segment portions 11; 11' extend in the forward direction over the transition point T1 and from the transition point T1 in an acute angle β. β is defined as the angle between the central line A and a tangent line of the circular segment portions 11; 11', where the tangent line is the tangent line at the transition point T1 of the respective circular segment portions 11; 11'. The angle β may be for 30-70°, 40-60°, or 45°.

The head core portion a1 further comprises in the first and second longitudinal portions I; II mirror imaged first edge lines 13; 13', to which the circular segment portions 11; 11' transition directly or indirectly via a smooth curved connection. The first edge lines 11; 11' are essentially straight or slightly arched. The core 3 has a first maximum width M1 in the head core portion a1before transition of the circular segment portions 11; 11' to the first tapering edge lines 13; 13'. The first maximum width M1 is from 35-50 mm, or from 36 to 40 mm. It is important that M1 has a sufficient width to ensure that the core is comfortable during use. The width M1 should be sufficient to cover the labia, while the width should be small enough to not to extend outside the edges of the intended underwear. The width above has been found to fulfil these requirements. The circular segment portions 11; 11' can transition to the first tapering edge lines 13; 13' at the first maximum width M1 of head core portion a1 or below the first maximum width M1 of the head core portion a1. From the transition the first edge lines 13; 13' taper towards an intermediate core portion a2 and towards the central line A of the core in an angle α, α being from 15-45°. A larger angle than 45° leads to a broad head portion which may not completely fit within the crotch portion of the brief. A smaller angle than 15° leads to a narrow head core portion a1 which may not have enough absorption capacity or coverage to ensure that discharge of fluids does not reach the briefs as well as the comfort during use is impaired. The first edge lines 13; 13' taper to second transition points T2, T2' located between the head core portion a1 and the intermediate core portion a2. The distance between the second transition points T2; T2' is the width M2 of the core 3. M2 is from 20-34 mm, or from 24 to 28 mm.

The intermediate core portion a2 includes in the respective first and second longitudinal portions I; II mirror imaged first convex edge portions 15; 15' extending between the second transition points T2; T2' and third transition points T3; T3'. The third transition points T3; T3' are located between the intermediate core portion a2 and the rear core portion a3. The length of the convex edge portions 15; 15' in respect to the central line A is from 50-60% of the total length of the central line A of the core and have a maximum height h1; h1' of the arch in the transverse direction of the core of from 1-10 mm. The total length of the convex edges 15; 15' is thus determined by the distance D1; D1' between the second transition points T2; T2' and the third transition points T3; T3' in the direction along the central line A and the maximum height h1; h1'. The maximum height h1; h1' is measured from a longitudinally extending line coinciding with the distance D1; D1' to the highest point on the convex edges 15; 15'. The location of the maximum height h1; h1' coincides with the location of the second maximum width M3 of the intermediate core portion a2. It is important that M3 has a sufficient width to ensure that a maximum amount of the discharge lands on the core and not outside the core during use, while the width should be small enough to not to extend outside the edges of the intended underwear. In this way leakage problems can be avoided. The transition between the first edge lines 13; 13' and the first convex edge portions 15; 15' can be a continuous, smooth transition. The transition between the first edge lines 13; 13' and the first convex edge portions 15; 15' can alternatively be a discontinuous transition, i.e. a transition in which the first edge lines 13; 13' and the first convex edge portions 15; 15' form a notch at the transition.

The rear core portion a3 includes second edge lines 17; 17' extending between the third transition points T3; T3' and fourth transition points T4; T4'. The second edge lines 17; 17' are essentially straight or slightly arched. The transition between the first convex edge portions 15; 15' and the second edge lines 17; 17' can be a continuous, smooth transition. The second edge lines 17; 17' taper towards a rear end T5 and the central line A of the core in an angle γ. The angle γ is defined as the angle between an extension of the distance D1 passing through transition point T3; T3' and a tangent line of the first convex edge portions 15; 15', where the tangent line is the tangent line at the transition point T3; T3' of the respective first convex edge portions 15; 15'. The angle may be for example 3-20°, 5-15°, or 7-11°. The second edge lines 17; 17' taper to a fourth transition point T4, T4' from which the second edge lines 17; 17' transition to a rear end portion 19 that joins the edge lines 17; 17' together. In a particular embodiment shown in FIG. 1, the rear end portion 19 is semi-circular or has a shape of a circular segment. However, the end rear portion could have a straight line connecting the second edge lines 17; 17'. The transition between the second edge lines 17; 17' and the semi-circular or circular segment rear end portion 19 can be a continuous, smooth transition. The total length of the core 3 between the first transition point T1 and the rear end T5 of the core 3 is from 100 to 150 mm, from 120 to 135 mm, or from 126 to 131 mm.

The absorbent core 3 can also have rounded edges for increased comfort.

Reference signs mentioned in the claims should not be seen as limiting the extent of the matter protected by the claims, and their sole function is to make claims easier to understand.

The drawings and the description are to be regarded as illustrative in nature, and not restrictive.

The invention claimed is:

1. An absorbent product comprising:
  a liquid-permeable top layer;
  a liquid-impermeable bottom layer;
  an absorbent core arranged between the top layer and the bottom layer, the absorbent core comprising an absorbent material with absorbent characteristics and a superabsorbent material;
  a first extension in a longitudinal direction;
  a second extension in a transverse direction;
  a longitudinal central line extending through the absorbent product and located between a first longitudinal portion and a second longitudinal portion of the absorbent product, which first and second longitudinal portions are symmetrical about the longitudinal central line;
  a head product portion, an intermediate product portion and a rear product portion extending in a longitudinal direction of the absorbent product, wherein the intermediate product portion comprises an area with a smaller width than any area in the head product portion and rear product portion, respectively; and
  an outer product contour having a shape resembling an hourglass,
  wherein the core extends in the longitudinal direction and transverse direction of the absorbent product and has an outer core contour of the core that is asymmetrical with the outer product contour;
  wherein the head product portion comprises:
    a foremost product point of the absorbent product in the longitudinal direction at the point where the central line of the absorbent product crosses the outer product contour;
    a first product width extending between two opposing outermost product points on the outer product contour in the transverse direction, the first product width being the greatest width in the absorbent product;
    a first core width extending between two opposing outermost core points of the outer core contour in the transverse direction, the first core width being the greatest width in the core,
  wherein the head product portion transitions to the intermediate product portion at two opposing intermediate product transition points on the outer product contour and two opposing intermediate core transition points on the outer core contour,
  wherein the core has a second core width in transverse direction extending between the two opposing intermediate core transition points, the second core width being smaller than the first core width,
  wherein the intermediate product portion comprises:
    a second product width extending between two opposing innermost product points on the outer product contour in the transverse direction, the second product width being the smallest width, which second product width is longitudinally distanced from the second core width; and
    a third core width extending between two opposing outermost intermediate core points on the outer core contour of the intermediate core portion, the third core width being the greatest width in the absorbent core rearward of the second core width;
  wherein the intermediate product portion transitions to the rear product portion at rear product transition points on the outer product contour and rear core transition points on the outer core contour,
  wherein the rear product portion comprises:
    a third product width which has the greatest width in the absorbent product rearward of the second product width; and
    a rear core portion tapering towards a rear core end point, which is the point along the outer core contour the most rearward in the longitudinal direction and which is longitudinally distanced from a rear product end point of the absorbent product, which is the point along the outer product contour the most rearward in the longitudinal direction,
  wherein the rear product portion contains a point on the outer product contour, which has the largest distance to the outer core contour, and
  wherein the third core width is longitudinally closer to the second product width than to the third product width.

2. The absorbent product according to claim 1, wherein a ratio of a thickness of an edge area of the absorbent product between the outer product contour and outer core contour and a thickness of the core is from 1:35 to 1:3.

3. The absorbent product according to claim 2, wherein the thickness of the core is from 1.5 to 3.4 mm and the thickness of the edge area of the absorbent product is 0.1 to 0.3 mm.

4. The absorbent product according to claim 1, wherein the outer product contour is an asymmetrical hourglass-shaped contour, wherein the outer product contour comprises, in the intermediate product portion, a first concave arch-shaped portion having a first radius which transitions to a second arch-shaped portion having a second radius, and wherein the first radius is smaller than the second radius.

5. The absorbent product according to claim 1, wherein the top layer comprises a nonwoven material, being a spunbond material comprising polypropylene fibres.

6. The absorbent product according to claim 1, wherein the head core portion comprises, in the respective first and second longitudinal portions, mirror imaged:
  a. first circular segment portions extending in a longitudinally forward direction of the core from a core transverse transition point, located on the central line between the first circular segment portions, in an acute angle β between the central line and a tangent at the core transverse transition point in respect of the circular segment portion; and
  b. first edge lines, to which the circular segment portions transition, tapering towards the intermediate core portion and towards the central line of the core in an angle α being from 15-45°, wherein the first edge lines taper to the intermediate core transition points located between the head core portion and the intermediate core portion.

7. The absorbent product according to claim 1, wherein the intermediate core portion comprises, in the respective first and second longitudinal portions, mirror imaged first convex edge portions extending between the intermediate core transition points and the outer core transition points which are located between the intermediate core portion and the rear core portion, wherein the convex edge portions have a length of from 50-60% of the total length of the central line and have a maximum height of the arch in the transverse direction of the core of from 1-10 mm.

8. The absorbent product according to claim 1, wherein the rear core portion comprises second edge lines tapering towards the rear core end point and the central line of the core in an angle γ being from 3-15°, and wherein the second edge lines taper to a second edge line transition point from which the second edge lines transition to a semi-circular or circular segment rear end portion that joins the second edge lines together.

9. The absorbent product according to claim 1, wherein a total length of the absorbent product between the foremost product point and the rear product end point is from 130 to 175 mm.

10. The absorbent product according to claim 1, wherein a longitudinal extension of the head product portion is about ⅓ of an extension of the absorbent product along the central line, a longitudinal extension of the intermediate product portion is about ⅓ of the extension of the absorbent product along the central line and a longitudinal extension of the rear product portion is about ⅓ of the extension of the absorbent product along the central line.

11. The absorbent product according to claim 1, wherein a longitudinal extension of the head product portion along the central line is from 40 to 50 mm, a longitudinal extension of the intermediate product portion along the central line is about 45-60 mm and a longitudinal extension of the rear product portion along the central line is about 40-50 mm of the extension of the absorbent product.

12. The absorbent product according to claim 1, wherein the first product width of the absorbent product in the head product portion is from 64-72 mm.

13. The absorbent product according to claim 1, wherein the second product width in the intermediate product portion is from 42-50 mm.

14. The absorbent product according to claim 1, wherein the third product width in the rear product portion of the absorbent product is from 55 to 63 mm.

15. The absorbent product according to claim 1, wherein the superabsorbent material in the core is in an amount from 10 to 30% by weight of the total weight of the core.

16. The absorbent product according to claim 1, wherein the core has a density from about 100 to 180 $kg/m^3$.

17. The absorbent product according to claim 1, wherein the core comprises cellulosic fluff pulp, tissue, absorbent foam materials or absorbent nonwoven materials as the absorbent material.

18. The absorbent product according to claim 1, wherein an area of the absorbent product in which the core is positioned is embossed with a pattern that principally follows the design of the core.

19. The absorbent product according to claim 1, wherein the bottom layer comprises a sprayed adhesive coating on the side facing away from the body facing side of the absorbent product on which a release paper is attached.

\* \* \* \* \*